US011491268B1

(12) United States Patent
Dabel (10) Patent No.: US 11,491,268 B1
(45) Date of Patent: Nov. 8, 2022

(54) MECHANICAL KIDNEY TRANSPLANT

(71) Applicant: Pascal Dabel, Los Angeles, CA (US)

(72) Inventor: Pascal Dabel, Los Angeles, CA (US)

(*) Notice: Subject to any disclaimer, the term of this patent is extended or adjusted under 35 U.S.C. 154(b) by 504 days.

(21) Appl. No.: 16/743,236

(22) Filed: Jan. 15, 2020

(51) Int. Cl.
*A61M 1/16* (2006.01)
*A61M 1/36* (2006.01)
(Continued)

(52) U.S. Cl.
CPC ........ *A61M 1/1621* (2014.02); *A61M 1/1607* (2014.02); *A61M 1/1652* (2014.02); *A61M 1/1694* (2013.01); *A61M 1/267* (2014.02); *A61M 1/3601* (2014.02); *A61M 1/361* (2014.02); *A61M 1/3609* (2014.02); *A61M 1/3615* (2014.02); *A61M 1/3621* (2013.01); *A61M 1/3626* (2013.01); *A61M 1/3638* (2014.02); *A61M 1/3639* (2013.01); *A61M 1/3672* (2013.01); *A61M 1/3679* (2013.01); *A61M 5/142* (2013.01); *B01D 61/30* (2013.01); *B01D 63/02* (2013.01); *A61M 2205/3303* (2013.01); *A61M 2205/3324* (2013.01); *A61M 2205/3344* (2013.01); *A61M 2205/3368* (2013.01); *A61M 2205/3584* (2013.01); *A61M 2210/1085* (2013.01); *B01D 2311/25* (2013.01); *B01D 2311/2676* (2013.01)

(58) Field of Classification Search
CPC .. A61M 5/142; A61M 5/1621; A61M 5/1607; A61M 5/1652; A61M 5/1694; A61M 5/267; A61M 5/3601; A61M 5/3609; A61M 5/361; A61M 5/3615; A61M 5/3621; A61M 5/3626; A61M 5/3638; A61M 5/3639; A61M 5/3672; A61M 5/3679; A61M 2205/3303; A61M 2205/3324; A61M 2205/3344; A61M 2205/3368; A61M 2205/3584; A61M 2210/1085; B01D 61/30; B01D 63/02; B01D 2311/25; B01D 2311/2676
See application file for complete search history.

(56) References Cited

U.S. PATENT DOCUMENTS

| 4,247,393 A | * | 1/1981 | Wallace | A61M 1/3679 210/321.89 |
| 4,581,141 A | * | 4/1986 | Ash | A61M 1/3687 210/502.1 |

(Continued)

*Primary Examiner* — John Kim
(74) *Attorney, Agent, or Firm* — Dunlap Bennett & Ludwig, PLLC (57) ABSTRACT

A mechanical kidney transplant designed may include a four modules designed to interconnect to clean blood. The first module may include a plurality of pump modules and a resin gel regeneration module, wherein the first module is operatively attached to a patient's iliac artery, iliac vein, and bladder. The second module may be operatively attached to the first module and may include storage and pump systems. The third module may be operatively attached to the first and fourth modules and may include a housing with ports for inflow/outflow of the blood and the physiologic resin gel between the first module and the fourth module. The fourth module may include at least one dialyzer fiber sized to accommodate a volume of blood flowing therethrough and an area surrounding the dialyzer fiber may be sized to accommodate a volume of a physiologic resin gel flowing counter current to the blood.

10 Claims, 4 Drawing Sheets

(51) Int. Cl.
*A61M 5/14* (2006.01)
*B01D 61/30* (2006.01)
*B01D 63/02* (2006.01)
*A61M 5/142* (2006.01)
*A61M 1/26* (2006.01)

(56) References Cited

U.S. PATENT DOCUMENTS

2010/0100027 A1* 4/2010 Schilthuizen ....... A61M 1/3486
 210/287
2019/0328952 A1* 10/2019 Gerber ............... B01J 20/28014

* cited by examiner

MECHANICAL KIDNEY TRANSPLANT

BACKGROUND

The embodiments described herein relate generally to medical devices, and more particularly, to a mechanical kidney transplant.

Many patients suffer from kidney disease and ultimately end up on hemodialysis. Their quality of life is poor, and dialysis (both hemo and peritoneal) is very costly. Additionally, it does not clean the blood constantly like a real kidney, so life expectancy is less than 10 years for the majority of patients. The patient also has a resulting increase risk for infection, along with the pain and suffering caused by the catheters, arterio-venous fistulas, and needles/sticks/punctures.

Unfortunately, there are also not enough kidney transplants for everyone who needs one. As a result, the majority wait on the list for years, do not qualify for a transplant, and ultimately die while receiving dialysis.

Even for those who are lucky enough to receive a kidney transplant, the procedure requires medications that suppress the immune system, increasing the risk of cancer and infection. There is also the risk of disease recurrence—meaning the same disease that killed the original kidneys could come back and kill the transplanted kidney.

Therefore, what is needed is a mechanical kidney transplant that is similar to a kidney transplant, requires no immune suppression, has a decreased risk of infection and cancer, and disease recurrence cannot effect, wherein the transplant works 24 hours a day, 7 days a week to provide blood that is cleaner than blood going through dialysis, wherein the mechanical kidney transplant uses a physiologic resin gel to replace dialysate used in hemodialysis.

SUMMARY

Some embodiments of the present disclosure include a mechanical kidney transplant designed to accept unclean blood from the iliac artery, clean blood in the mechanical kidney transplant, and provide clean blood to the iliac vein. The mechanical kidney transplant may include a four modules designed to interconnect to clean the blood and produce waste as urine. The first module may include a plurality of pump modules and a resin gel regeneration module, wherein the first module is operatively attached to a patient's iliac artery, iliac vein, and bladder. The second module may be operatively attached to the first module and may include storage and pump systems. The third module may be operatively attached to the first and fourth modules and may include a housing with ports for inflow/outflow of the blood and the physiologic resin gel between the first module and the fourth module. The fourth module may include at least one dialyzer fiber sized to accommodate a volume of blood flowing therethrough and an area surrounding the dialyzer fiber may be sized to accommodate a volume of a physiologic resin gel flowing counter current to the blood. When the fourth module is attached to the third module, the mechanical kidney transplant may be in a blood kidney mode. When the fourth module is disengaged from the third module, the mechanical kidney transplant may be in bypass mode.

BRIEF DESCRIPTION OF THE FIGURES

The detailed description of some embodiments of the invention is made below with reference to the accompanying figures, wherein like numerals represent corresponding parts of the figures.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as a mechanical kidney transplant and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

The various elements of the present disclosure may be related in the following exemplary fashion. It is not intended to limit the scope or nature of the relationships between the various elements and the following examples are presented as illustrative examples only.

Figures 1, 2, 3:
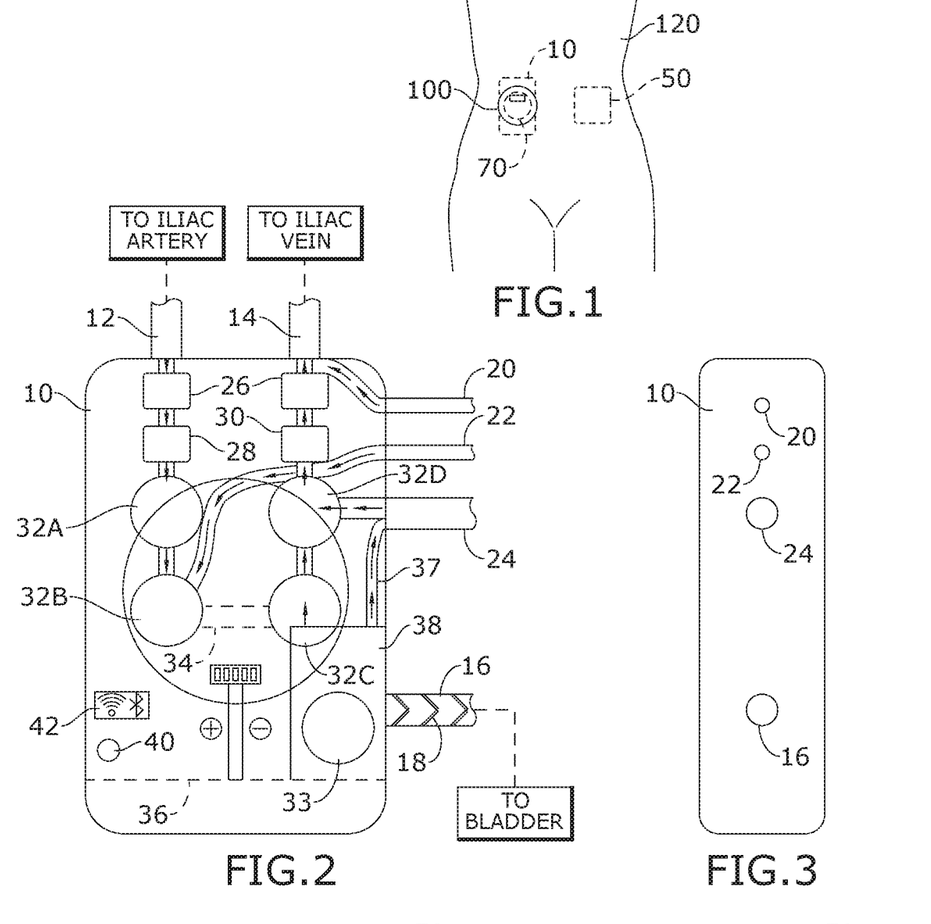
FIG. 1 is a schematic view of one embodiment of the present disclosure, showing the placement of parts.
FIG. 2 is a front schematic view of one embodiment of the present disclosure.
FIG. 3 is a side schematic view of one embodiment of the present disclosure.

By way of example, and referring to FIGS. 1-13 some embodiments of the invention include a mechanical kidney transplant comprising a plurality of modules operatively connected to one another, wherein blood flows from the iliac artery through the arterial line 12 into the modules and out of the modules through the venous line 14, wherein the entering blood is uncleaned and the exiting blood is cleaned. Placement of the modules in a patient 120 is shown in FIG. 1.

The first module may comprise a first module housing 10 designed to house the components of the first module. Specifically, a plurality of pump modules, such as four pump modules 32A, 32B, 32C, 32D, may be positioned within the first module housing 10. An arterial line 12 may extend from the first module housing 10 and be designed to attach to the iliac artery. A venous line 14 may extend from the first module housing 10 and be designed to attach to the iliac vein. A ureteral line 16 may extend from the first module housing 10 and be designed to attach to the bladder. Thus, unclean arterial blood may flow from the iliac artery through the arterial line 12 and into the first module housing 10 for processing. While inside the first module housing, the blood may first flow through a pressure and resistance monitor 26 and a urea nitrogen sensor 28 before entering a first pump module 32A.

If the device is in bypass mode, the blood may simply flow from the first pump module 32A (blood flow rate from about 50 to 100 mL/min) to the second pump module 32B (blood flow rate from about 50 to 100 mL/min) through the blood bypass line 34 to the third pump module 32C (blood flow rate from about 50 to about 100 mL/min) to the fourth pump module 32D (blood flow rate from about 100 to 200 mL/min), through an air sensor and trap 30 and a pressure and resistance monitor 26 and ultimately out of the first module housing 10 through a venous line 14 and to the iliac vein. While in the second pump module 32B, the blood 124 may mix with an anticoagulant, wherein the anticoagulant is pumped from an anticoagulation pump 58 and storage area in the second housing 50 through an anticoagulation pump line 22 into the first module housing 10 and to the second pump module 32B. As a result, when the device is in bypass mode, the blood may be mixed with an anticoagulant before being pumped back into the patient's body to prevent the blood from clotting. The device may be automatically placed into bypass mode when the fourth module housing 100 is disengaged from the third module housing 70.

Figure 10:
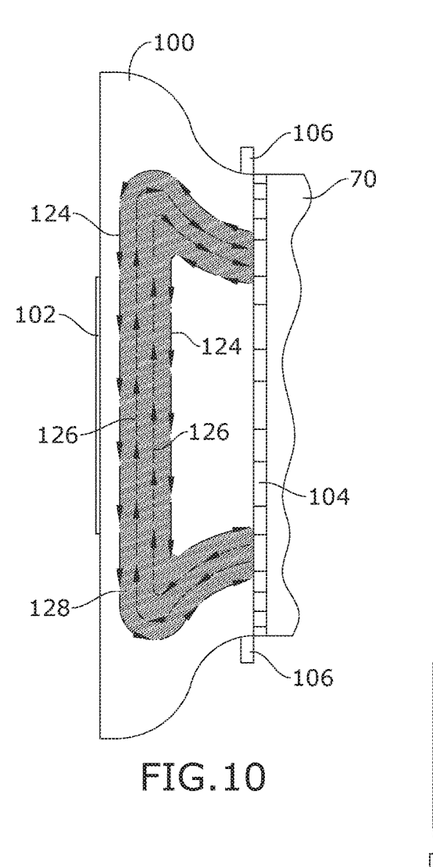
FIG. 10 is a flow chart describing one embodiment of the present disclosure.

If the device is in cleaning mode, the blood may flow from the first pump module 32A towards the arterial blood port 76 in the third module housing 70 into the dialyzer via the blood in port 112 in the fourth module housing 100. The blood flow rate (BFR) exiting the first pump module 32A may be from about 50 to about 100 mL/min. From the blood in port 112, the blood 126 may flow through the fourth module housing 100 as shown in FIG. 10, wherein the fourth module housing 100 contains a plurality of dialyzer fibers 128, and the blood flows through the dialyzer fibers 128. Resin gel 124 may also flow through the fourth housing module 100 in a countercurrent direction as compared to the blood 126, wherein the waste mixed with the blood 126 may move through semipermeable fibers 128 from the blood via osmosis, diffusion, and convection into the resin gel 124. Thus, removal of impurities from the blood 126 may take place within the fourth housing module 100. Cleaned blood 126 may flow out of the fourth housing through the blood out port 114 through the venous blood port 78 in the third module housing 70 and to the third pump module 32C. The cleaned blood 126 may ultimately flow from the third pump module 32C through the air sensor and trap 30 and the pressure and resistance monitor 26 to the venous line 14 and ultimately to the iliac vein. In some embodiments, the cleaned blood 126 may be mixed with epogen in the venous line 14. In such embodiments, the second module housing 50 may include an epogen pump 60 and storage area, wherein the epogen flows from the epogen pump through an epogen pump line 20 and into the first housing module 10 to mix with the cleaned blood 126 in the venous line 14.

While the blood 126 is circulating through the device, resin gel 124 may be simultaneously circulating through the device, wherein the resin gel 124 functions to pull impurities and waste from the blood to create waste/urine that flows from a resin gel regeneration module through a ureteral line 16 to the patient's bladder. The ureteral line 16 may include at least one one-way valve 18 positioned therein to prevent backflow of the urine back into the device.

Specifically, resin gel 124 may be regenerated/cleaned in the resin gel regeneration module 38, which may be positioned within the first module housing 10. A resin gel pump 33 may pump clean resin gel 124 from the resin gel module 38 through a clean resin gel return line 37 to the fourth pump module 32D. Physiologic resin gel may also be pumped into the fourth pump module 32D from a physiologic resin gel pump 52 positioned within the second module housing 50 through a physiologic resin gel pump line 24 into the fourth pump module 32D. From the fourth pump module 32D, the clean resin gel may be pumped toward the physiologic resin gel inflow 74 on the third housing module 70 and then into the fourth module housing 100 through the resin gel in port 108. From the in port 108, the resin gel 124 may flow through the fourth housing module 100 in a direction counter current to the blood flow 126, resulting in the waste being pulled from the blood into the resin gel, as explained above. Dirty resin gel may exit the fourth module housing through the resin gel out port 110 and through the third housing module 70 via the physiologic resin gel out flow 72. In embodiments, both the physiologic resin gel in flow 74 and the physiologic resin gel out flow 72 may include resin gel conductivity sensors 73, 75, wherein the resin gel conductivity sensors may measure the electrolyte concentration in the resin gel entering and leaving the third module housing 70. From the physiologic resin gel outflow 72 the dirty resin gel may be pumped to resin gel regeneration module 38. Within the resin gel regeneration module 38, the dirty resin gel may undergo cleaning and/or centrifugation to separate the waste from the resin gel. The cleaned resin gel may be returned to the physiologic resin gel pump and storage area 52 in the second module housing 50 via the physiologic resin gel pump line 24, wherein the waste may be pushed out of the resin gel regeneration module 38 into the ureteral line 16 as urine.

As mentioned above, the first housing module 10 may house the various pump modules 32A,B,C,D and the resin gel regeneration module 38. The first housing module 10 may also include other features, such as a temperature sensor 40, a Wi-Fi/Bluetooth module 42, and a backup battery 36. The Wi-Fi/Bluetooth module 42 may allow for communication from the device of the present disclosure to an external device, such as a smart phone, laptop computer, tablet computer, desktop computer, or other electronic device, wherein the external device may control functions of the system, such as turning it on and off, starting and stopping the cleaning or bypass functions, increasing or decreasing volume removal, and increasing or decreasing epogen/anticoagulation/resin gel rates. Based on different information sensed or otherwise collected by the various sensors within the system, the Wi-Fi/Bluetooth module 42 may send data (pressure, temperature, urea nitrogen levels, and the like) and provide for an alerting system and troubleshooting for a user.

Figure 12:
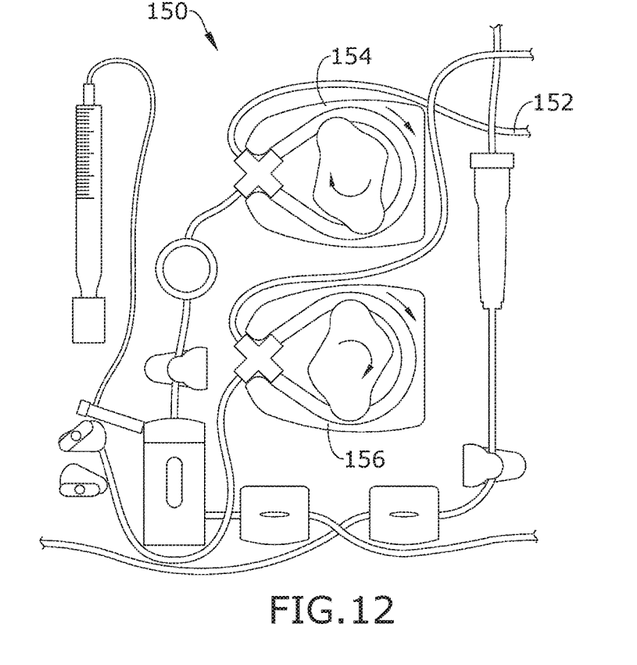
FIG. 12 is a schematic view of one embodiment of the present disclosure.

FIG. 12 shows a schematic view of a hemodialysis machine 150 including both a blood pump 154 and a dialysate pump 156 and a blood transport tubing 152. The pump modules 32A,B,C,D within the first module housing 10 may have a similar structure. While the pump modules 32 A,B,C,D may be similar in structure to the machine shown in FIG. 12, the use of other suitable pump structures are also envisioned.

Figure 4:
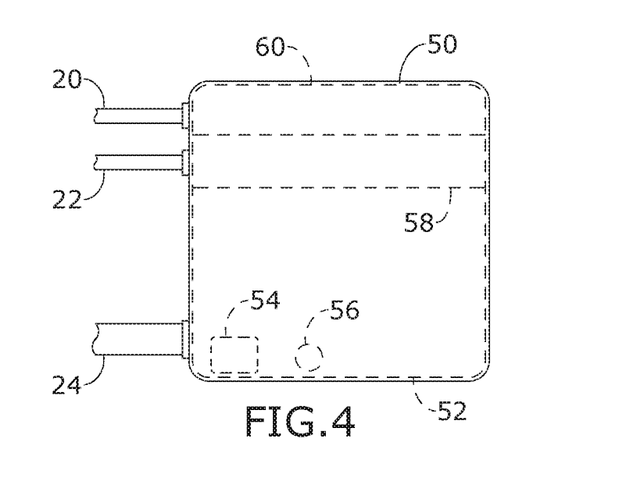
FIG. 4 is a front schematic view of one embodiment of the present disclosure.
Figure 5:
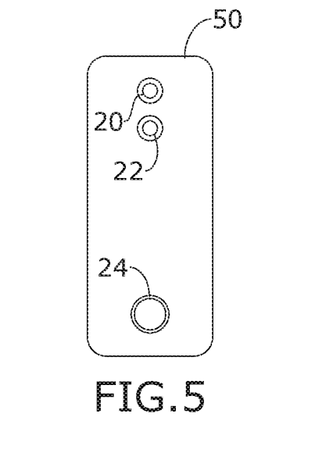
FIG. 5 is a side schematic view of one embodiment of the present disclosure.
Figure 6:
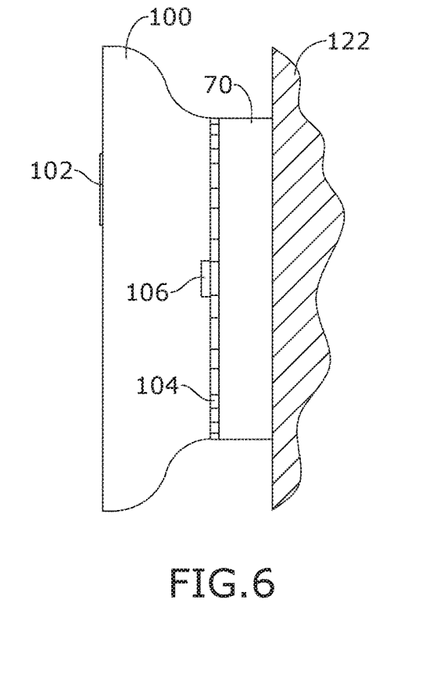
FIG. 6 is a side schematic view of one embodiment of the present disclosure, showing placement on the patient's skin.

As shown in FIG. 4, the second housing module 50 may comprise a plurality of storage and pump systems. For example, the second housing module 50 may include an epogen pump 60 and storage area, an anticoagulation pump 58 and storage area, and a physiologic resin gel pump 52 and storage area. Each of the storage areas may be attached to their respective area of the first module housing 10 via a pump line. For example, the epogen pump 60 and storage area may attach to the venous line 14 via an epogen pump line 20, the anticoagulation pump 58 and storage area may attach to the second pump module 32B via an anticoagulation pump line 22, and the physiologic resin gel pump 52 and storage area may attach to the fourth pump module 32D via a physiologic resin gel pump line 24. The physiologic resin gel storage area may include a urea nitrogen sensor 54 and a pH sensor 56 positioned therein. When the urea nitrogen sensor 54 senses a nitrogen level of more than 150 mg/dL or the pH sensor senses a pH lower than 6 or higher than 8, the user may be alerted either by the Wi-Fi/Bluetooth module 42 or another alert, such as a display on a display screen 102 attached to an outer surface of the fourth module housing 100. The epogen pump 60, the anticoagulation pump 58, and the physiologic resin gel pump 52 may each also monitor the volume of their respective solution remaining and alert a user when the volume gets too low. When the levels get too low, the storage areas may be refilled through injection ports in the third module housing 70, described in more detail below.

Figure 7:
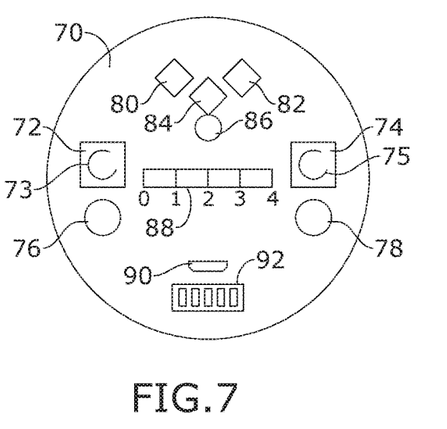
FIG. 7 is a front schematic view of one embodiment of the present disclosure.
Figure 8:
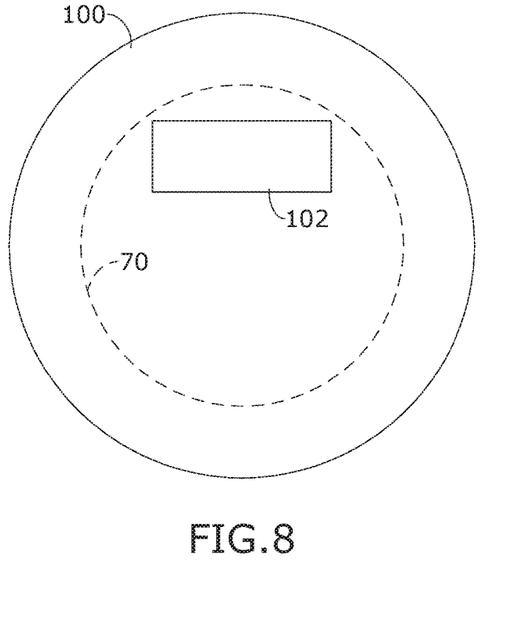
FIG. 8 is a front schematic view of one embodiment of the present disclosure.
Figure 9:
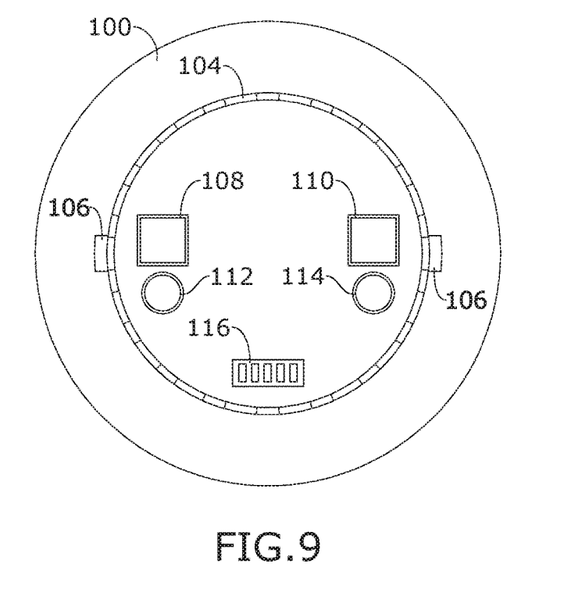
FIG. 9 is a rear schematic view of one embodiment of the present disclosure.

As shown in FIG. 7, the third module housing 70 may contain ports for the inflow/outflow of blood between the first module housing 10 and the fourth module housing 100 and for the inflow/outflow of physiologic resin gel between the first module housing 10 and the fourth module housing 100. The third module housing 70 may also include an anticoagulation injection port 80 operatively attached to the anticoagulation pump 58 and storage area for refilling anticoagulant, an erythropoietin stimulating agent injection port 82 operatively attached to the epogen pump 60 and storage area for refilling epogen, and a physiologic resin gel adjustment fluid injection port 84 for refilling/changing/draining the physiologic resin gel pump 52 and storage area. The third module housing 70 may also include a venous air trap release 86 operatively attached to the air sensor and trap 30 in the first module housing 10, wherein the venous air trap release 86 allows for releasing of excess air from blood returning to the body. The third module housing 70 may also include a charging port 90 operatively attached to the backup battery 36 in the first module housing 10, wherein the charging port 90 may be operatively connected to a charging cable to charge the backup battery 36. Lastly, the third module housing 70 may include an external battery contact 92 designed to removably engage with a battery 116 in the fourth module housing 100.

Figure 11A:
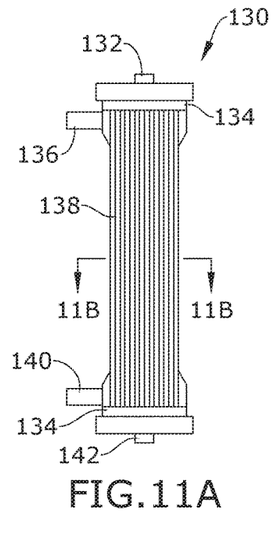
FIG. 11A is a schematic view of one embodiment of the present disclosure.
Figure 11B:
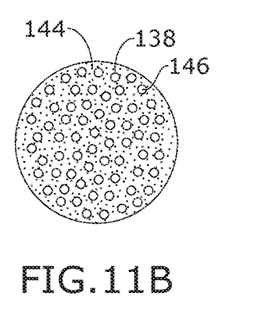
FIG. 11B is a cross-sectional schematic view of one embodiment of the present disclosure, taken along line 11B-11B in FIG. 11A.

As shown in FIGS. 6 and 8-10, the fourth module housing 100 may be attached to the third housing module 70 and be positioned outside of the patient's skin 122. The fourth module housing 100 may include a front surface with a display screen 102 attached thereto. The display screen 102 may display any status or information from the system, as collected by the various sensor and electrical components. A surface of the fourth module housing 100 opposite the front surface may include the resin gel in port 108, the resin gel out port 110, the blood in port 112, the blood out port 114, and the battery 116. These components may operatively attach to components on the front surface of the third module housing 70 as described above. As shown in FIG. 10, the interior of the fourth module housing 100 may comprise the dialyzer fibers 128 through which the untreated blood flows 126. The resin gel 124 may flow around the fiber casing in a counter current flow, causing waste from the blood 126 to transfer into the resin gel 124 to clean the blood 126. In some embodiments, the dialyzer fibers 128 may have a structure similar to that of a basic hemofilter 130, as shown in FIGS. 11A and 11B. For example, each fiber 128 may comprise a hollow fiber membrane 138 with a substantially cylindrical shape with a physiologic resin gel in port 140 positioned at a first end proximate to a blood out port 142 and an effluent out port 136 positioned at a second end proximate to a blood in port 132. Potting 134 may be positioned at either end thereof. As shown in FIG. 11B, blood may flow through small fibers 146 while the physiologic resin gel 144 flows through the area surrounding the small fibers 146, wherein the fibers are semipermeable such that waste from the blood may flow therethrough into the physiologic resin gel 144.

As shown in FIG. 10, the fourth module housing 100 may be removably attached to the third module housing 70 by a locking system. In a particular embodiment, the locking system may include an air/water tight magnet lock system 104. When the locking system is engaged, the back surface of the fourth module housing 100 may securely attach to the front surface of the third module housing 70, completing a blood cleaning circuit and, as a result, causing the resin gel in port 108 to engage with the physiologic resin gel inflow 74, the resin gel out port 100 to engage with the physiologic resin gel outflow 72, the battery 116 to engage with the external batter contact 92, the blood out port 114 to engage with the venous blood port 78, and causing the blood in port to engage with the arterial blood port 76. When the fourth module housing 100 is attached to the third module housing 70, blood and resin gel may flow from the first module housing 10 to the fourth module housing 100 for the cleaning of the unclean blood. The fourth module housing 100 may be disengaged from the third module housing 70 using a release, such as lock release 106, which may cause the locking system to disengage. When the fourth module housing 100 is removed from the third module housing 70, the bypass may be activated, as described above. Additionally, the removal of the fourth module housing 100 may allow for access to the injection ports on the third module housing 70 to add or remove the substances from the second module housing 50. It may also allow for the ability to change the battery and other repair or troubleshooting.

As described above, the system of the present disclosure may use a physiologic resin gel for cleaning and purification of the blood. While any suitable resin gel may be used, in some embodiments, the resin gel may comprise agarose beads with a physiological composition, such that the gel does not absorb waste or water but attracts it such that it is removed from the blood. An example of a suitable resin gel is described in co-pending U.S. patent application Ser. No. 16/676,872, the entire contents of which is herein incorporated by reference.

Figure 13:
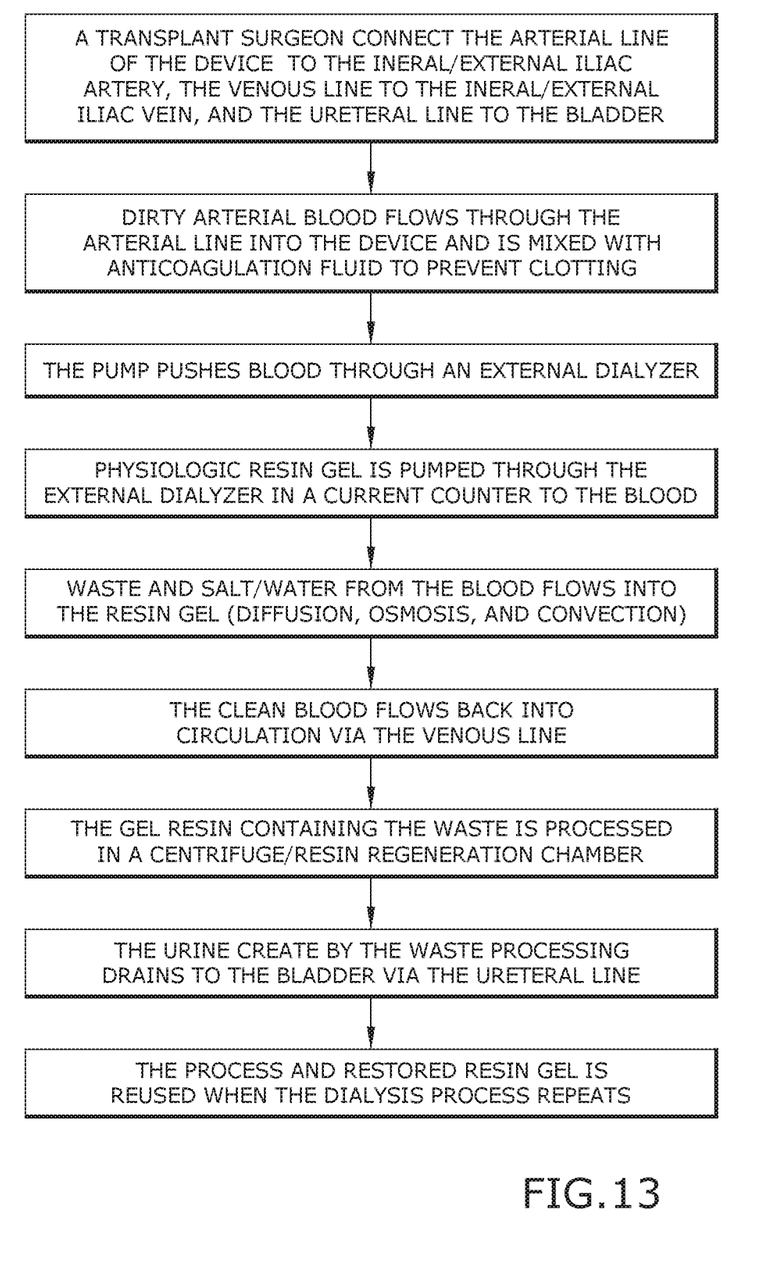
FIG. 13 is a flow chart explaining one embodiment of the present disclosure.

As described in FIG. 13, use of the system of the present disclosure may include the following steps. First, a transplant surgeon may connect the arterial line of the device to the internal/external iliac artery, the venous line to the internal/external iliac vein, and the ureteral line to the bladder. Then, dirty arterial blood may flow through the arterial line into the device, where it is mixed with anticoagulation fluid to prevent clotting. A pump module may push the blood through an external dialyzer (fourth module housing 100). Simultaneously, physiologic resin gel may be pumped through the external dialyzer in a counter current flow to the blood. Waste and salt/water from the blood may flow into the resin gel via diffusion, osmosis, and convection. The clean blood may then flow back into circulation via the venous line, and the gel resin containing the waste may be processed in the centrifuge/resin regeneration chamber. The urine created by the waste processing may drain to the bladder via the ureteral line. The process and restored resin gel may be reused when the dialyses process repeats.

As such, the mechanical kidney transplant of the present disclosure may allow patients to come off of dialysis and have an improved quality of life and cleaner blood, resulting in improved life expectancy. In fact, the mechanical kidney transplant may function similar to a human kidney transplant without requiring the use of immunosuppressive medications/drugs, while lessening the risk for infection and cancer, and while being immune to disease recurrence. Because the mechanical kidney transplant may work 24 hours a day, 7 days a week, blood is cleaner than that cleaned via dialysis treatments, which are intermittent.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A mechanical kidney transplant designed to clean blood, the mechanical kidney transplant comprising:
    a first module comprising:
        a first module housing;
        a plurality of pump modules positioned within the first module housing;
        a resin gel regeneration module positioned within the first module housing;
        an arterial line extending from the first module housing, the arterial line having a first arterial end designed to attach to a patient's iliac artery and a second arterial end operatively attached to the plurality of pump modules;
        a venous line extending from the first module housing, the venous line having a first venous end operatively attached to the plurality of pump modules and a second venous end designed to attach to the patent's iliac vein; and
        a ureteral line extending from the first module housing, the ureteral line having a second ureteral end designed to attach to the patient's bladder;
    a second module operatively attached to the first module, the second module comprising a plurality of storage and pump systems;
    a third module operatively attached to the first module; and
    a fourth module comprising a fourth module housing operatively attached to the third module, the fourth module housing comprising an interior comprising at least one dialyzer fiber sized to accommodate a volume of blood flowing therethrough and an area surrounding the at least one dialyzer fiber sized to accommodate a volume of a physiologic resin gel,
    wherein:
        the third module comprises a third module housing containing ports for inflow/outflow of the blood and the physiologic resin gel between the first module housing and the fourth module housing.

2. The mechanical kidney transplant of claim 1, wherein the plurality of pump modules comprises a first pump module, a second pump module, a third pump module, and a fourth pump module.

3. The mechanical kidney transplant of claim 2, wherein the plurality of storage and pump systems comprise:
    an epogen pump and storage area operatively attached to the venous line via an epogen pump line, the epogen pump and storage area sized to accommodate a volume of epogen;
    an anticoagulation pump and storage area operatively attached to the second pump module via an anticoagulation pump line, the anticoagulation pump and storage area sized to accommodate a volume of anticoagulant; and
    a physiologic resin gel pump and storage area operatively attached to the fourth pump module via a physiologic resin gel pump line, the physiologic resin gel pump and storage area sized to accommodate a volume of the physiologic resin gel.

4. The mechanical kidney transplant of claim 3, wherein the third module housing further comprises:
    an anticoagulation injection port operatively attached to the anticoagulation pump and storage area;
    an erythropoietin stimulating agent injection port operatively attached to the epogen pump and storage area; and
    a physiologic resin gel adjustment fluid injection port operatively attached to the physiologic resin gel pump and storage area.

5. The mechanical kidney transplant of claim 1, wherein the physiologic resin gel flows in a direction counter current to flow of the blood in the interior of the fourth module housing.

6. The mechanical kidney transplant of claim 5, wherein the at least one dialyzer fiber comprises:
    a hollow fiber membrane with a substantially cylindrical shape;
    a physiologic resin gel in port positioned at a first end of the hollow fiber membrane proximate to a blood out port; and
    an effluent out port positioned at a second end of the hollow fiber membrane proximate to a blood in port.

7. The mechanical kidney transplant of claim 6, further comprising a plurality of small fibers positioned within the hollow fiber membrane, wherein the small fibers are semi-permeable such that waste from the blood flows through the small fibers into the physiologic resin gel.

8. The mechanical kidney transplant of claim 1, further comprising:
    a pressure and resistance monitor and a urea nitrogen sensor attached to the arterial line between the first arterial end and the plurality of pump modules; and
    an air sensor and trap and a pressure and resistance monitor attached to the venous line between the plurality of pump modules and the second venous end,
    wherein:
        the third module housing further comprises a venous air trap release operatively attached to the air sensor and trap.

9. The mechanical kidney transplant of claim 1, wherein:
    the fourth module housing is removably attached to the third module housing by a locking system;
    when the locking system is engaged, a back surface of the fourth module housing is securely attached to a front surface of the third module housing, completing a blood cleaning circuit that provides for cleaning of blood; and when the locking system is disengaged, the back surface of the fourth module housing is released from the front surface of the third module housing, breaking the blood cleaning circuit and placing the mechanical kidney transplant in bypass mode.

10. The mechanical kidney transplant of claim 9, wherein the locking system comprises an air/water tight magnet lock system with a lock release.

* * * * *